| United States Patent [19] | [11] Patent Number: 4,588,695 |
|---|---|
| Takano et al. | [45] Date of Patent: May 13, 1986 |

[54] DETERMINATION OF UNSATURATED IRON-BINDING CAPACITY

[75] Inventors: Susumu Takano, Nagaokakyo; Yoshikey Yoneda, Matsubara, both of Japan

[73] Assignee: Wako Pure Chemical Industries, Ltd., Osaka, Japan

[21] Appl. No.: 654,292

[22] Filed: Sep. 25, 1984

[30] Foreign Application Priority Data

Sep. 26, 1983 [JP] Japan .................. 58-177505

[51] Int. Cl.⁴ .................. G01N 33/90
[52] U.S. Cl. .................. 436/87; 436/74; 436/84; 436/910
[58] Field of Search .................. 436/74, 84, 87, 910

[56] References Cited

U.S. PATENT DOCUMENTS

| 3,095,382 | 6/1963 | Hach | 436/84 |
| 3,537,822 | 11/1970 | O'Malley et al. | 436/74 |
| 3,925,020 | 12/1975 | Ogawa et al. | 436/910 X |

OTHER PUBLICATIONS

Schade et al., Chemical Abstracts, vol. 49, 1954, No. 3297b, p. 1955.
Kotelyanskaya et al., Chemical Abstracts, vol. 77, 1972, No. 83210g, p. 599.
Gradwohl's Clinical Laboratory Methods & Diagnosis, vol. 1, 8th edition, 1980, C. V. Mosby Co., St. Louis, Missouri, pp. 849-854.
Schade et al., Proc. Soc. Exp. Biol. & Med. 87, 443-448, (1954).

*Primary Examiner*—Arnold Turk
*Attorney, Agent, or Firm*—Armstrong, Nikaido, Marmelstein & Kubovcik

[57] ABSTRACT

Unsaturated iron-binding capacity in serum can be measured colorimetrically rapidly and easily by using an auto analyzer and using a reagent mixture comprising excess iron ions, a reducing agent for iron ions, and a hydroxy acid and/or a salt of a hydroxy acid together with a color-forming reagent solution.

9 Claims, 3 Drawing Figures

DETERMINATION OF UNSATURATED IRON-BINDING CAPACITY

BACKGROUND OF THE INVENTION

This invention relates to a process for measuring an unsaturated iron-binding capacity in serum. More particularly, this invention relates to an improved process for measuring an unsaturated iron-binding capacity in serum rapidly and easily by using a special buffering agent which has weak coordinate bonding strength particularly with iron while having suitable bonding properties with iron in the case of using a chelate color-forming reagent.

Iron exists in a living body as hemoglobin in a red blood corpuscle in an amount of about ⅔ of iron and as stored iron in an amount of the rest ⅓ of iron in the liver, the spleen, the bone-marrow, and the like. The total weight of iron in a human body is about 4 g. The iron is lost in an amount of about 1 mg per day by peeling of mucous membrane from the intestine, removal of the skin, and the like and is hardly lost by excretion of urine. Therefore, the balance can be maintained by absorbing about 1 mg of iron from food every day. All the iron in serum is physiologically bound to transferrin which is a kind of globulin and is transferred. Transferrin is a kind of protein having a molecular weight of about 90,000 and has a capacity to bind two iron atoms per mole in the ferric form. Transferrin is generally present in serum in the form of the so-called serum iron wherein transferrin binds iron in an amount of ⅓ thereof and the rest ⅔ is present as transferrin not binding iron. The amount of transferrin not binding iron is measured as the unsaturated iron-binding capacity in serum.

Such iron in serum and the unsaturated iron-binding capacity relate to the metabolism of hemoglobin and the measurement of such items is indispensable for a differential diagnosis of anemic persons.

There have practically been used various methods for measuring the unsaturated iron-binding capacity which has a clinically important meaning. For example, there is a method wherein a minute amount of iron is gradually added for direct photoelectric colorimetry by using a principle that iron-transferrin produces a pink color [the Rath and Finch method: J. Clin. Invest, 28, 79–85 (1949)]. But this method is disadvantageous in that it is necessary to use a large amount of sample serum. There is also a method comprising adding an excess iron to serum, adsorbing iron not bound to transferrin by adding a magnesium carbonate powder thereto, separating the magnesium carbonate by a centrifugal separating procedure, and measuring the iron in a supernatant liquid [the Ramsay method: Clin. Chim. Acta, 2, 221–226 (1957)]. But this method is complicated and disadvantageous. There is also a method wherein radioactive $Fe^{59}$ is used, but since a non-sealed isotope is used, the use of it is very limited.

On the other hand, there is a method comprising adding an alkaline buffer solution to serum, adding iron to the mixture to bind transferrin to iron, and colorimetrically determining the residual iron to measure the unsaturated iron-binding capacity [the Schade method: Proc. Soc. Exp. Biol. & Med., 87, 443–448 (1954)]. More in detail, the Schade method comprises adding 1.0 ml of serum to 2.0 ml of a 1.0M tris buffer solution (pH=8.1), allowing the resulting mixture to stand for 5 minutes, adding 1.0 ml of an ammonium ferrous sulfate solution (3.51 mg/dl) containing 0.5% by weight of ascorbic acid to the resulting mixture, measuring absorbance at 535 nm by using a photoelectric colorimeter (blank), adding a drop of 0.5% bathophenanthroline sulfonic acid-$Na_2$ salt for color formation, allowing to stand at 25° C. for 10 minutes or more, and measuring absorbance at 535 nm. It is said that serum iron releases iron from transferrin at pH 4.0 or lower while the bonding between iron and transferrin is strong and stable at the alkaline side. But when a chelate color-forming reagent such as bathophenanthroline is added, dissociation of transferrin and iron begins to take place at about pH 7.0 or lower. But when the pH is 7.5 or higher, no dissociation of transferrin and iron takes place even if bathophenanthroline is present. Therefore, according to the Schade method, it is essential to conduct the measurement at the pH of 7.5 or higher. On the other hand, the color-forming reaction rate is maximum at about pH 5.0 in the case of using bathophenanthroline as a color-forming reagent. The color-forming rate is slowed down when the pH is either higher or lower than that pH (about 5.0). When bathophenanthroline is used as a color-forming reagent in the Schade method, it is necessary to make the pH of the solution about 7.5 to 8.5 considering the stability of serum iron. But when pH=8.1 is selected in practice, it takes about 10 minutes for the color formation. Thus, the shortening of the color-formation in the Schade method is demanded strongly in order to use an auto analyzer, although the Schade method is a very simple method without using centrifugal separation, removal of proteins and complicated procedures.

SUMMARY OF THE INVENTION

It is an object of this invention to provide a process for measuring unsaturated iron-binding capacity in serum with a short time in color formation using a special buffer solution.

This invention provides a process for measuring an unsaturated iron-binding capacity in serum which comprises:

adding to serum a reagent mixture comprising excess iron ions in a known amount, a reducing agent for iron ions, and at least one member selected from the group consisting of hydroxy acids and salts of hydroxy acids as acid component, adding a color-forming reagent to the resulting mixture, and measuring the amount of unreacted iron ions colorimetrically.

DESCRIPTION OF THE PREFERRED EMBODIMENTS

This invention is characterized by the use of the special reagent mixture as a buffer solution (an iron-containing buffer solution). The present inventors have studied extensively the causes for prolonging of the time necessary for the color formation and found that a special buffer solution is effective for shortening the time necessary for color formation.

That is, in general, the strength of a coordinate bond of iron is different depending on the ligands. It is observed that $O^- > N$ in the case of $Fe^{III}$ and $O^- \cong N$ in the case of $Fe^{II}$ (K, Ueno, et. al: "Metal Chelate I" p.23, published by Nanko-do Co., 1965). But these are not always constant and change depending on other conditions. The present inventors have found that carboxylic acids having O ligands have weaker chelate bonding strength with iron when used as a buffer agent than conventionally used trishydroxymethylaminomethane (a tris buffer) having an N ligand. Further, it was also found that a hydroxy acid shows special properties which were not shown by other carboxylic acids; that is, a hydroxy acid has weaker chelate bonding strength with iron than trishydroxymethylaminomethane but has adequate bonding properties with iron. When such a hydroxy acid is used as a buffer agent, the time required for the color formation is remarkably shortened. This is clearly shown in FIG. 1.

Figure 1:
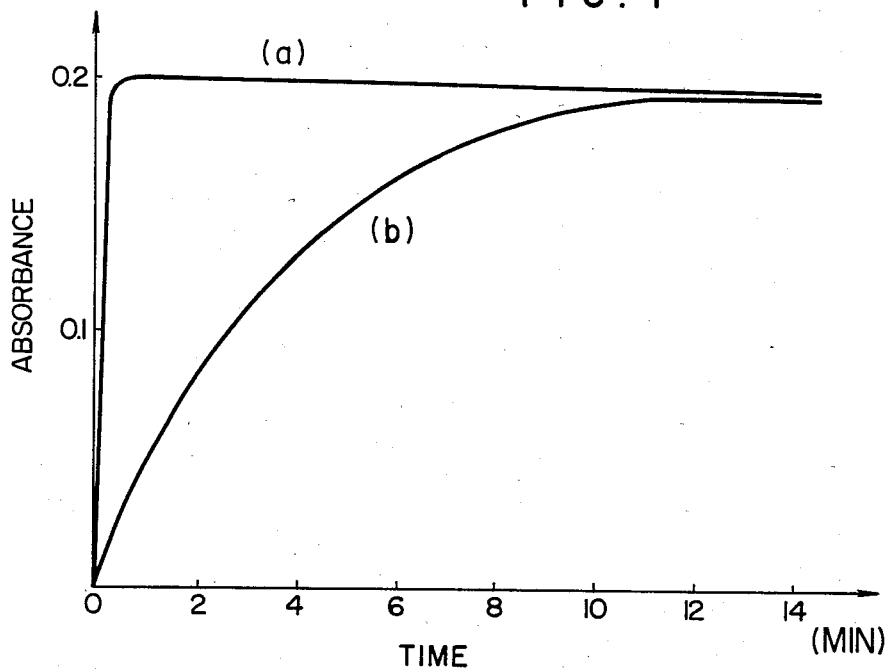
FIG. 1 is a graph showing a difference in color-forming reaction time between the Schade method and this invention.

FIG. 1 is a graph showing a difference in color-forming reaction time between the process of this invention (the curve (a)) and the Schade method (the curve (b)). As clearly shown in FIG. 1, the color-forming reaction is completed in several tens of seconds according to the process of this invention. In contrast, according to the Schade method, a time of 10 minutes or more is necessary to complete the color-forming reaction. That the time of 10 minutes or more is necessary for the color formation is a fatal defect in application to an auto analyzer.

Figure 2:
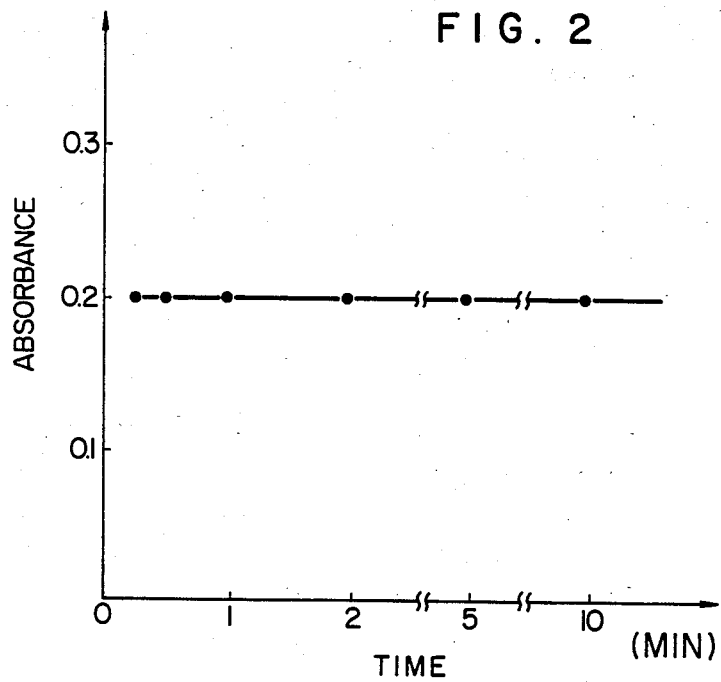
FIG. 2 is a graph showing a saturation time of transferrin by iron according to this invention.

FIG. 2 is a graph showing a saturation time of transferrin by iron according to this invention. More in detail, when a buffer solution including excess iron ions as used in Example 1, that is, a tartrate buffer solution is added to serum, and a color-forming reagent solution is added thereto after 0.25, 0.5, 1, 2, 5 or 10 minutes, there is no change in absorbance whether the color-forming reagent solution is added after 15 seconds or 10 minutes. This means that unsaturated transferrin is in a saturated state in several seconds.

As mentioned above, by using a hydroxy acid as a buffer solution, it becomes possible to bind transferrin to iron atoms in several seconds and iron ions not bound to transferrin can be color-formed in several or several tens seconds and the color-forming reaction can be completed in less than a several minutes.

The reagent mixture used as a buffer solution (iron-containing buffer solution) comprises excess iron ions, a reducing agent for iron ions and at least one member selected from the group consisting of hydroxy acids and salts of hydroxy acids as an acid component.

Since iron ions are bound to transferrin in serum, it is necessary to use iron ions in excess amount but the amount should already be known. As a source for iron ions, there can be used water-soluble iron salts such as ammonium ferrous sulfate, etc.

As the reducing agent for iron ions, there can be used ascorbic acid and alkali metal (Li, K, Na) salts of ascorbic acid.

As the hydroxy acids, there can be used aliphatic hydroxy acids and aromatic hydroxy acids. As the salts of hydroxy acids, there can be used salts (e.g. Na, K, and the like alkali metal salts) of these hydroxy acids. Examples of hydroxy acids are glycolic acid, lactic acid, α-hydroxybutyric acid, glyceric acid, tartronic acid, malic acid, tartaric acid, citric acid, mandelic acid, etc. These hydroxy acids and salts thereof can be used alone or as a mixture thereof.

The pH of the iron-containing buffer solution is preferably adjusted in the range of 7.5 to 9.5, more preferably 8.0 to 8.5. The molar concentration of a hydroxy acid and/or a salt of a hydroxy acid contained in the iron-containing buffer solution is, as a total, preferably in the range of 0.05 to 0.4 mole/l (M), more preferably 0.08 to 0.2 M.

The iron-containing buffer solution can be prepared, for example, by adding to 600 ml of water 20 ml of 1N hydrochloric acid, 10 ml of ammonium ferrous sulfate solution (obtained by dissolving 20 to 80 mg of ammonium ferrous sulfate $FeSO_4(NH_4)_2SO_4 \cdot 6H_2O$ in 100 ml of 1N HCl), 0.08 to 0.2 M of a hydroxy acid and/or a salt of a hydroxy acid, and 0.005 to 0.1 M of sodium tetraborate ($Na_2B_4O_7 \cdot 10H_2O$), adjusting the pH with an acid or alkali, and making the whole volume 1 liter with water. At the time of use, ascorbic acid is dissolved so as to be included in an amount of 0.5 to 1.0% W/V to make the iron-containing buffer solution.

As the color-forming reagent, there can be used bathophenanthroline (BPT), α,α'-dipyridyl, o-phenanthroline, 2,4,6-tripyridyl-S-triazine (TPTZ), 3-(2- pyridyl)-5,6-bis(4-sulfophenyl)-1,2,4-triazine (PDTS), nitrosophenol derivatives such as 2-nitroso-5-(N-propyl-N-sulfopropylamino)phenol, etc.

According to this invention, the iron-containing buffer solution comprising excess iron ions with known amounts, a reducing agent for iron ions and at least one member selected from hydroxy acids and salts of hydroxy acids is added to a serum sample, followed by color formation to measure the amount of unreacted iron ions colorimetrically by a conventional process.

In recent years, various auto analyzers have been introduced in the field of clinical examinations. But according to the Schade method, since the time necessary for the color formation is too long to apply to an auto analyzer, it has generally been believed that the unsaturated iron-binding capacity cannot be measured by an auto analyzer. But in contrast to such a common knowledge, it becomes possible to measure the unsaturated iron-binding capacity by using an auto analyzer rapidly and easily according to this invention.

This invention is illustrated by way of the following Examples, in which all percents are by weight unless otherwise specified.

EXAMPLE 1

An iron-containing buffer solution was prepared by adding to 600 ml of water, 20 ml of 1N HCl, 10 ml of ammonium ferrous sulfate obtained by dissolving 40 mg of ammonium ferrous sulfate in 100 ml of 1N HCl, 28.1 g of sodium potassium tartrate and 7.62 g of sodium tetraborate ($Na_2B_4O_7 \cdot 10H_2O$), adjusting the pH to 8.5 with 1N HCl, making the whole volume 1 liter with water, and dissolving ascorbic acid so as to be included in an amount of 0.5% W/V.

As a color-forming reagent solution, there was used a 0.2% bathophenanthroline sulfonic acid-$Na_2$ salt solution.

On the other hand, control serum was prepared by gradual dilution of control serum with an unsaturated iron-binding capacity of 800 μg/dl to give different unsaturated iron-binding capacities of 200, 400 and 600 μg/dl, respectively.

To 3.5 ml of the iron-containing buffer solution, 0.2 ml of a control serum was added and mixed, followed by measurement of absorbance at 535 nm (Absorbance $E_{s\cdot 1}$). Then, 0.5 ml of the color-forming reagent solution was added thereto and mixed, and the resulting mixture was allowed to stand at room temperature for several minutes. Then, absorbance at 535 nm was measured (Absorbance $E_{s\cdot 2}$).

The above-mentioned procedures were repeated using 0.2 ml of water as blank, or 0.2 ml of iron standard solution containing 200 μg/dl of $Fe^{2+}$, in place of the control serum to give absorbances of $E_{Bl\cdot 1}$ (Bl: blank), $E_{st\cdot 1}$ (st: standard), $E_{Bl\cdot 2}$ and $E_{st\cdot 2}$, respectively.

Figure 3:
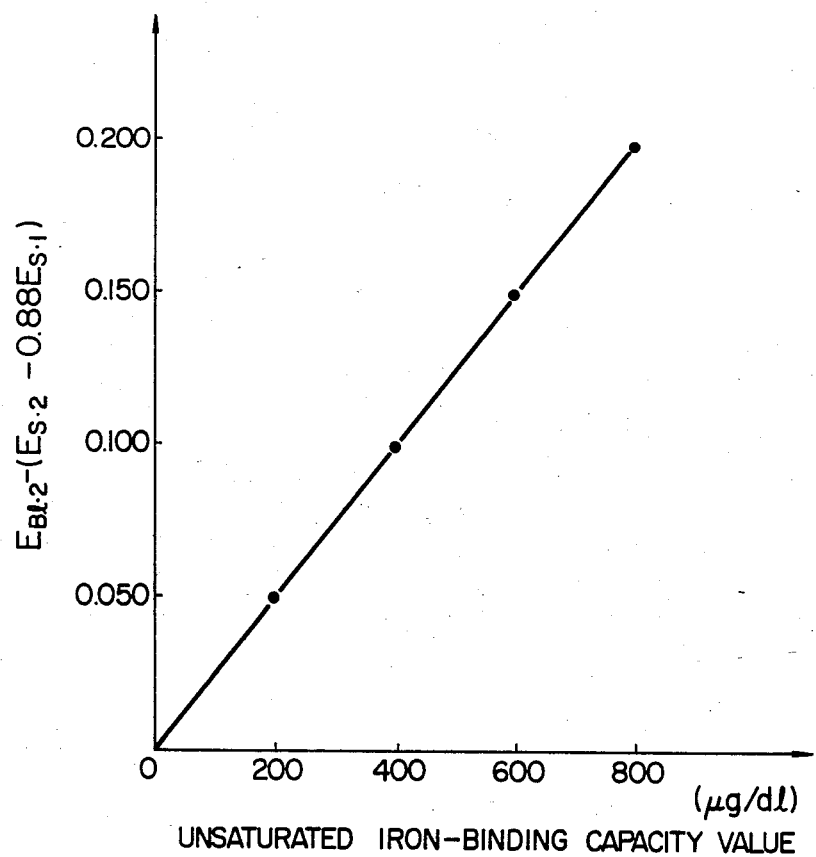
FIG. 3 shows a calibration curve obtained in Example 1.

A calibration curve obtained by connecting absorbance differences $[E_{Bl\cdot 2}-(E_{s\cdot 2}-0.88\ E_{s\cdot 1})]$ plotted against each unsaturated iron-binding capacity of each control serum (μg/dl) shows a linear line started from the zero point as shown in FIG. 3 and shows good quantitativeness.

EXAMPLE 2

To 3.5 ml of the same iron-containing buffer solution as used in Example 1, 0.2 ml of serum sample was added and mixed to measure absorbance at 535 nm (Absorbance $E_{s\cdot 1}$). Subsequently, 0.5 ml of the same color-forming reagent solution as used in Example 1 was added thereto and mixed, and the resulting mixture was allowed to stand at room temperature for several minutes. Then, absorbance at 535 nm was measured (Absorbance $E_{s\cdot 2}$).

The above-mentioned procedures were repeated using 0.2 ml of water as blank, or 0.2 ml of iron standard solution containing 200 μg/dl of $Fe^{2+}$, in place of the serum sample to give absorbances of $E_{Bl\cdot 1}$, $E_{st\cdot 1}$, $E_{Bl\cdot 2}$ and $E_{st\cdot 2}$, respectively.

From the measured absorbances, the value of $E_{Bl\cdot 2}-(E_{s\cdot 2}-0.88\ E_{s\cdot 1})$ was obtained and the unsaturated iron-binding capacity in the serum sample was obtained by using the calibration curve obtained in Example 1.

Alternatively, the unsaturated iron-binding capacity can be calculated by inserting the absorbances $E_{s\cdot 1}$, $E_{s\cdot 2}$, $E_{Bl\cdot 2}$ and $E_{st\cdot 2}$ into the following equation:

Unsaturated iron-binding capacity (μg/dl) =

$$\frac{E_{Bl.2} - (E_{s.2} - 0.88\ E_{s.1})}{E_{st.2} - E_{Bl.2}} \times 200$$

wherein the value of 0.88 is a coefficient for correcting the liquid amount.

REFERENCE EXAMPLE 1

[Magnesium Carbonate Precipitation Method (Conventional Method A)]

To 0.2 ml of a serum sample, 1 ml of a ferric chloride solution (Fe 0.5 μg/ml) was added and vibrated softly for mixing, followed by standing at room temperature for about 5 minutes. Then, 0.15 g of magnesium carbonate was added thereto and 0.5 ml of distilled water was also added and mixed, followed by standing at room temperature for 30 minutes. After centrifugal treatment, 2.0 ml of a buffer solution (5% sodium lauryl sulfate-0.1 M acetate buffer, pH 6.0) and 15 mg of L-ascorbic acid were added to 0.5 ml of the supernatant liquid, followed by addition of one drop of 0.2% bathophenanthroline sulfonic acid-$Na_2$ salt solution. After allowing to stand at room temperature for 5 minutes, absorbance at 535 nm was measured to give a total iron-binding capacity. On the other hand, a serum iron value was measured by a conventional method. The unsaturated iron-binding capacity was obtained by subtracting the serum iron value from the total iron-binding capacity.

The values of unsaturated iron-binding capacity obtained by Example 2 and Reference Example 1 are shown in Table 1. As is clear from Table 1, the values of Example 2 are in good agreement with those of Reference Example 2.

TABLE 1

| Serum sample No. | Example 2 (Y) | Reference Example 1 (X) |
|---|---|---|
| 1 | 250 μg/dl | 252 μg/dl |
| 2 | 375 | 370 |
| 3 | 400 | 395 |
| 4 | 330 | 335 |
| 5 | 222 | 220 |
| Average | 315.4 | 314.4 |

γ = 0.998
Y = 1.02X − 6.08

EXAMPLE 3

[Measurement by Using Auto Analyzer]

An iron-containing buffer solution was prepared by adding to 600 ml of water, 20 ml of 1N HCl, 10 ml of ammonium ferrous sulfate obtained by dissolving 40 mg of ammonium ferrous sulfate in 100 ml of 1N HCl, 13.4 g of malic acid and 7.62 g of sodium tetraborate ($Na_2B_4O_7\cdot 10H_2O$), adjusting the pH to 8.0 with 1N HCl, making the whole volume 1 liter with water, and dissolving ascorbic acid so as to be included in an amount of 0.5% W/V.

To 20 μl of a serum sample, 350 μl of the iron-containing buffer solution was added and incubated at 37° C. for 4 minutes 40 seconds. Subsequently, absorbance at 546 nm was measured. After 20 seconds, 50 μl of the same color-forming reagent solution as used in Example 1 was added thereto. After 5 minutes, absorbance at 546 nm was measured. The auto analyzer used was Hitachi 705 Type Auto Analyzer manufactured by Hitachi, Ltd.

On the other hand, the unsaturated iron-binding capacity was measured by a conventional method B (the Nitroso PSAP color-forming method wherein Amberlite CG-400 mfd. by Rohm & Haas Co. was used as a precipitation assistant and 2-nitroso-5-(N-propyl-N-sulfopropylamino)-phenol (Nitroso-PSAP, a trade name) was used as a color-forming reagent) in a manual method. The results are shown in Table 2 in comparison with the results of Example 3.

TABLE 2

| Serum sample No. | Example 3 (Y) | Conventional method B (X) |
|---|---|---|
| 1 | 155 μg/dl | 176 μg/dl |
| 2 | 284 | 268 |
| 3 | 233 | 239 |
| 4 | 72 | 79 |
| 5 | 393 | 404 |
| 6 | 212 | 218 |
| 7 | 194 | 188 |
| 8 | 106 | 110 |
| 9 | 255 | 257 |
| 10 | 191 | 215 |
| Average | 209.5 | 215.4 |

γ = 0.992
Y = 1.008X − 7.61

As is clear from Table 2, the values of Example 3 are in good agreement with those of the conventional method B.

EXAMPLE 4

An iron-containing buffer solution was prepared by adding to 600 ml of water, 20 ml of 1N HCl, 10 ml of ammonium ferrous sulfate obtained by dissolving 40 mg of ammonium ferrous sulfate in 100 ml of 1N HCl, 7.6 g of glycolic acid and 7.62 g of sodium tetraborate ($Na_2B_4O_7 \cdot 10H_2O$), adjusting the pH to 8.2 with 1N HCl, making the whole volume 1 liter with water, and dissolving ascorbic acid so as to be included in an amount of 0.5% W/V.

As a color-forming reagent solution, there was used a 0.2% 3-(2-pyridyl)-5,6-bis(4-sulfophenyl)-1,2,4-triazine (PDTS) solution.

Using the same serum sample as used in Example 2, the unsaturated iron-binding capacity was obtained in the same manner as described in Example 2 by measuring absorbances at 560 nm.

The same results as obtained in Example 2 were obtained.

EXAMPLE 5

[Measurement by Using Auto Analyzer]

An iron-containing buffer solution was prepared by adding to 600 ml of water, 20 ml of 1N HCl, 10 ml of ammonium ferrous sulfate obtained by dissolving 80 mg of ammonium ferrous sulfate in 100 ml of 1N HCl, 10.8 g of lactic acid, and 7.62 g of sodium tetraborate ($Na_2B_4O_7 \cdot 10H_2O$), adjusting the pH to 8.2 with 1N HCl, making the whole volume 1 liter with water, and dissolving ascorbic acid so as to be included in an amount of 0.5% W/V.

As a color-forming reagent solution, there was used a 0.1% 2-nitroso-5-(N-propyl-N-sulfopropylamino)-phenol (Nitroso-PSAP) solution.

As an auto analyzer, there was used Hitachi 736 Type Auto Analyzer.

To 20 $\mu$l of the same serum sample as used in Example 3, 350 $\mu$l of the iron-containing buffer solution was added and incubated at 37° C. for 2 minutes 50 seconds. Subsequently, absorbance at 700 nm was measured. Then, 10 seconds later, 50 $\mu$l of the color-forming reagent solution was added thereto. After 4 minutes 30 seconds, the absorbance at 700 nm was measured.

The results were the same as those obtained in Example 3.

EXAMPLE 6

[Measurement by Using Auto Analyzer]

An iron-containing buffer solution was prepared by adding to 600 ml of water, 20 ml of 1N HCl, 10 ml of ammonium ferrous sulfate obtained by dissolving 40 mg of ammonium ferrous sulfate in 100 ml of 1N HCl, 7.6 g of glycolic acid and 7.62 g of sodium tetraborate ($Na_2B_4O_7 \cdot 10H_2O$), adjusting the pH to 8.5 with 1N HCl, making the whole volume 1 liter with water, and dissolving ascorbic acid so as to be included in an amount of 0.5% W/V.

As a color-forming reagent solution, there was used a 0.1% 2,4,6-tripyridyl-s-triazine (TPTZ) solution.

As an auto analyzer, there was used Nihon Denshi VX-1000 Type Auto Analyzer.

To 30 $\mu$l of the same serum sample as used in Example 3, 400 $\mu$l of the iron-containing buffer solution was added and incubated at 37° C. for 2 minutes 17 seconds. Then, absorbance at 600 nm was measured. Then, 12 seconds later, 100 $\mu$l of the color-forming reagent solution was added thereto and absorbance at 600 nm was measured after 2 minutes 24 seconds. The unsaturated iron-binding capacity was obtained in the same manner as described in Examples 3 and 5. The results were the same as those obtained in Examples 3 and 5.

In a conventional method, TPTZ is used at a pH range of 3 to 6, but according to the present invention, it can be used at pH 8.0 without losing its color-forming ability.

What is claimed is:

1. A process for measuring unsaturated iron-binding capacity in serum which comprises:

adding to serum a reagent mixture comprising iron ions in an amount in excess of the amount required to react with all unbound transferrin in the serum, a reducing agent for reducing $Fe^{3+}$ ions to $Fe^{2+}$ ions, and at least one acid component selected from the group consisting of hydroxy acids and salts of hydroxy acids, wherein the pH of said reagent mixture is 7.5 to 9.5, and the concentration of said acid component is 0.05 to 0.4 mole/liter, adding to the resulting mixture a reagent which forms a color with the excess unreacted iron ions, and measuring the amount of unreacted iron ions colorimetrically.

2. A process according to claim 1, wherein the acid component is at least one member selected from the group consisting of glycolic acid, lactic acid, α-hydroxybutyric acid, glyceric acid, tartronic acid, malic acid, tartaric acid, citric acid, mandelic acid and alkali metal salts of these hydroxy acids.

3. A process according to claim 1, wherein the color-forming reagent is bathophenanthroline, α,α'-dipyridyl, o-phenanthroline, 2,4,6-tripyridyl-s-triazine, 3-(2-pyridyl)-5,6-bis(4-sulfophenyl)-1,2,4-triazine, or 2-nitroso-5-(N-propyl-N-sulfopropylamino)phenol.

4. A process according to claim 1, wherein the acid component is a mixture of a hydroxy acid and an alkali metal salt of a hydroxy acid.

5. A process according to claim 4, wherein the mixture of a hydroxy acid and an alkali metal salt of a hydroxy acid is a mixture of at least one hydroxy acid selected from the group consisting of tartaric acid, malic acid, glycolic acid and lactic acid, and at least one sodium or potassium salt of a hydroxy acid selected from the group consisting of tartaric acid, malic acid, glycolic acid and lactic acid.

6. A reagent mixture comprising iron ions in an amount in excess of the amount required for reacting with all unbound transferrin in a serum sample, a reducing agent for iron ions, and at least one acid component selected from the group consisting of hydroxy acids and salts of hydroxy acids, wherein the pH of said reagent mixture is 7.5 to 9.5, and the concentration of said acid component is 0.05 to 0.4 mole/liter.

7. A reagent mixture according to claim 6, wherein the reducing agent for iron ions is ascorbic acid or an alkali metal salt thereof.

8. A reagent mixture according to claim 6, wherein the acid component is at least one member selected from the group consisting of glycolic acid, lactic acid, α-hydroxybutyric acid, glyceric acid, tartronic acid, malic acid, tartaric acid, citric acid, mandelic acid and alkali metal salts of these hydroxy acids.

9. A reagent mixture according to claim 6, wherein the acid component is a mixture of a hydroxy acid and an alkali metal salt of a hydroxy acid.

* * * * *